United States Patent [19]

Sjøholm et al.

[11] Patent Number: 5,714,369
[45] Date of Patent: Feb. 3, 1998

[54] FERVIDOBACTERIUM AMYLASE AND PULLULANASE

[75] Inventors: Carsten Sjøholm, Bagsværd, Denmark; Garabed Antranikian, Hamburg-Harburg, Germany

[73] Assignee: Novo Nordisk A/S, Bagsvaerd, Denmark

[21] Appl. No.: 704,638

[22] PCT Filed: Mar. 2, 1995

[86] PCT No.: PCT/DK95/00095

§ 371 Date: Sep. 9, 1996

§ 102(e) Date: Sep. 9, 1996

[87] PCT Pub. No.: WO95/23850

PCT Pub. Date: Sep. 8, 1995

[30] Foreign Application Priority Data

Mar. 4, 1994 [DK] Denmark ................................. 258/94

[51] Int. Cl.$^6$ .............................. C12N 9/28; C12N 1/20; C12P 7/06; C12P 19/14
[52] U.S. Cl. .................... 435/202; 435/252.1; 435/161; 435/99
[58] Field of Search ................. 435/201, 202, 435/95, 161, 170, 210, 98, 99

[56] References Cited

U.S. PATENT DOCUMENTS 4,929,557  5/1990  Antranikian et al. ................. 435/202

FOREIGN PATENT DOCUMENTS

92/16617  10/1992  WIPO .

OTHER PUBLICATIONS

Brown et al., "Characterization of Amylolytic Enzyme Activities Associated With The Hyperthermophilic Archaebacterium *Pyrococcus furiosus*", Applied And Environmental Microbiology, Jul. 1990, pp. 1985–1991.
Koch et al., "Purification And Properties Of A Hyperthermoactive α-amylase From The Archaeobacterium *Pyrococcus woesei*", Arch Microbiol. 1991, 155: pp. 572–578.
Dialog, file 357, Derwent Biotechnology Abs, DBA Accession No. 87-07485.
Antranikian et al., Chem. Ing. Tech., vol. 64, No. 6, pp. 548–550 (1992).
Medline—Accession No. 94079331.
Dialog, file 357, Derwent Biotechnology Abs, DBA Accession No. 94-13129.
Dialog, file 55, Biosis Previews, Dialog Accession No. 98081261.
Hartley et al. "Industrial prospects of thermophiles and thermophilic enzymes", Biochem. Soc. Symp. (1983) vol. 48, pp. 133–146.
Plant et al. "Starch degradation by thermophilic anaerobic bacteria," System Appl. Microbiol. (1987) vol. 9, pp. 158–162.
Madi et al. "Identification of a starch degrading anaerobic thermophile producing thermostable alpha–amylase and pullulanase", Appl. Microbiol. Biotechnol. (1989) vol. 30(4), pp. 422–425.

*Primary Examiner*—Jean C. Witz
*Assistant Examiner*—Susan Hanley
*Attorney, Agent, or Firm*—Steve T. Zelson, Esq.; Valeta Gregg, Esq.

[57] ABSTRACT

The present invention relates to Fervidobacterium amylase and pullulanase preparations and their use in producing sweeteners and ethanol from starch. In particular the enzymes are derived from *Fervidobacterium pennavorans*.

5 Claims, 2 Drawing Sheets

5,714,369

FERVIDOBACTERIUM AMYLASE AND PULLULANASE

CROSS-REFERENCE TO RELATED APPLICATIONS

This application is a 35 U.S.C. 371 national application of PCT/DK95/00095 filed Mar. 2, 1995, which is incorporated herein by reference.

FIELD OF INVENTION

The present invention relates to a novel thermostable amylase and a novel thermostable pullulanase and their use in the production of sweeteners and ethanol from starch.

BACKGROUND OF THE INVENTION

The production of sweeteners from starch has been largely improved by application of different microbial enzymes to obtain better quality and yields, but the necessity of performing several steps of the starch-hydrolysing process at elevated temperatures means that there is still a need for new starch-hydrolysing enzymes with increased thermal stability.

It is known that Pyrococcus, e.g. *Pyrococcus wosei* and *Pyrococcus furiosus*, for reference see *Arch. Microbiol.* 155, 1991, pp. 572–578, and *Appl. Env. Microbiol.* 56, 1990, pp.1985–1991, can produce highly thermostable amylases.

It is the object of this invention to provide an amylase and a pullulanase with temperature optimum at 80° C. or above 80° C.

SUMMARY OF THE INVENTION

We have unexpectedly found that a novel thermostable amylase can be obtained from the genus Fervidobacterium, a genus not previously reported to produce thermostable amylase; and a novel thermostable pullulanase which can be obtained from *Fervidobacterium pennavorans*; these new enzymes have temperature optimum around 80°–90° C.

Accordingly, the invention provides an amylase preparation, characterized by being producible by cultivation of an amylase producing strain of the genus Fervidobacterium, and a pullulanase preparation, characterized by being producible by cultivation of a pullulanase producing strain of *Fervidobacterium pennavorans*.

BRIEF DESCRIPTION OF DRAWINGS

The present invention is further illustrated by reference to the accompanying drawings, in which.

DETAILED DISCLOSURE OF THE INVENTION

The Microorganism

Figure 1:
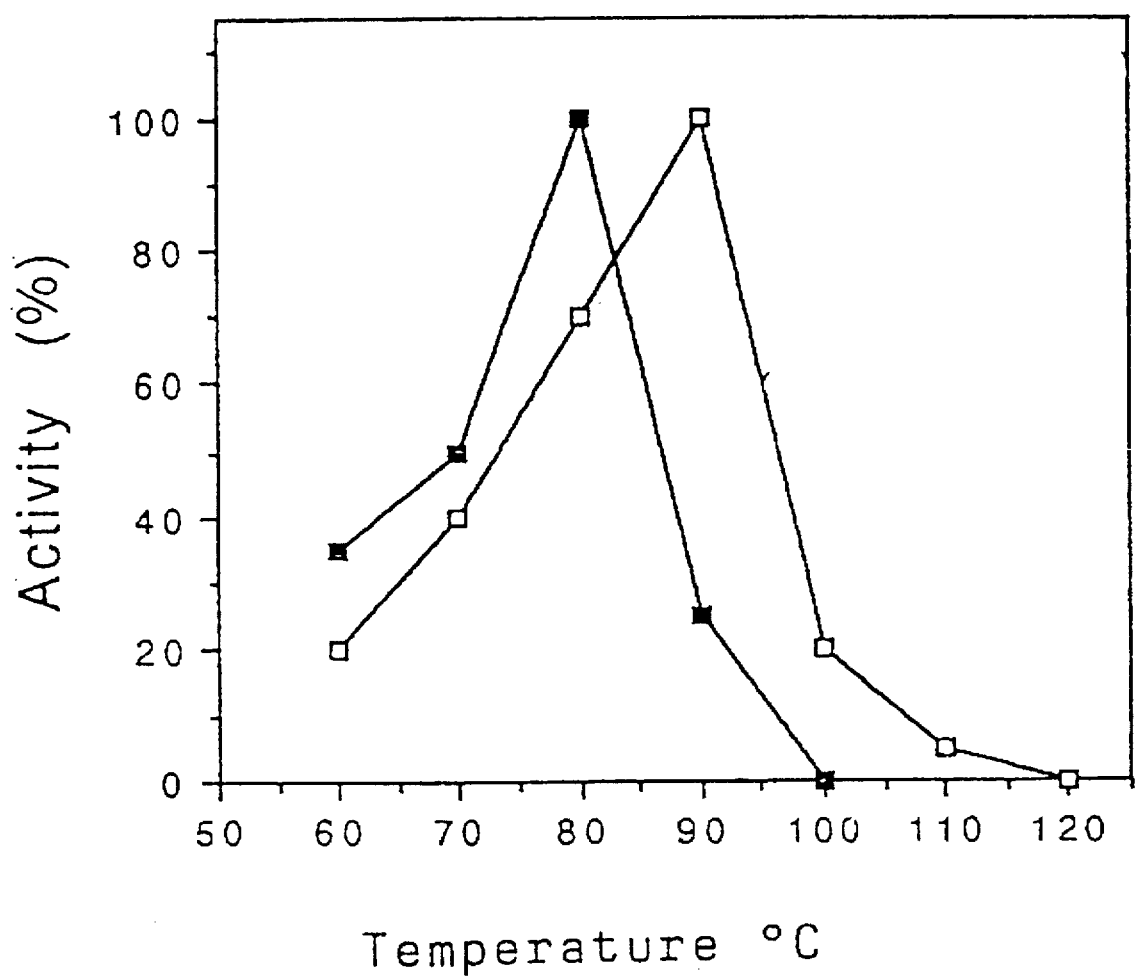
FIG. 1 shows the relative activity (% rel.) of an amylase (☐) and a pullulanase (■) of the invention at various temperatures (determined at pH 5.5 with starch and pullulan, respectively, as substrate).

According to the invention, amylase is derived from an amylase producing strain of the genus Fervidobacterium, in particular *Fervidobacterium pennavorans*, and pullulanase is derived from a pullulanase producing strain of *Fervidobacterium pennavorans*.

A strain representative of *Fervidobacterium pennavorans* has been deposited according to the Budapest Treaty on the International Recognition of the Deposits of Microorganisms for the Purpose of Patent Procedures, on 12 Mar., 1992, at Deutsche Sammlung von Microorganismen und Zellkulturen GmbH, under Accession No. DSM 7003.

Production of Amylase and Pullulanase

Amylase and pullulanase of the invention may be produced by anaerobic cultivation of the above mentioned strain on a nutrient medium containing suitable carbon and nitrogen sources, such media being known in the art. Anaerobic conditions may be achieved during the preparation of media by sparging with $N_2$ and following the anaerobic techniques as described by Balch and Wolfe in *Appl. Env. Microbiol.* 32, 1976, pp. 781–791.

Alternatively, amylase and pullulanase of the invention can be produced by aerobic cultivation of a transformed host organism containing the appropriate genetic information from the above mentioned strain. Such transformants can be prepared and cultivated by methods known in the art.

The amylase and the pullulanase may be recovered by removing the cells from the fermentation medium (e.g. by centrifugation or filtration) and then concentrating the broth (e.g. by ultrafiltration). If desired, the amylase and the pullulanase may be further purified by known methods.

Immunochemical Properties

The enzymes of the invention have immunochemical properties identical or partially identical (i.e. at least partially identical) to those of an enzyme derived from the strain *Fervidobacterium pennavorans*, DSM 7003.

The immunochemical properties can be determined immunologically by cross-reaction identity tests. The identity tests can be performed by the well-known Ouchterlony double immunodiffusion procedure or by tandem crossed immunoelectrophoresis according to Axelsen N. H.; Handbook of Immunoprecipitation-in-Gel Techniques; Blackwell Scientific Publications (1983), chapters 5 and 14. The terms "antigenic identity" and "partial antigenic identity" are described in the same book, Chapters 5, 19 and 20.

Monospecific antisera are generated according to the above mentioned method by immunizing rabbits with the purified enzymes of the invention. The immunogens are mixed with Freund's adjuvant and injected subcutaneously into rabbits every second week. Antisera are obtained after a total immunization period of 8 weeks, and immunoglobulins are prepared therefrom as described by Axelsen N. H., supra.

The Enzymes

An amylase of the invention can be characterized by having amylase activity at temperatures of from below 60° C. to approximately 120° C., having activity optimum at temperatures in the range 85°–95° C., determined at pH 5.5 with starch as substrate. The amylase can also be characterized by having amylase activity at pH values of from below pH 4.5 to approximately pH 9.8, having optimum in the range pH 5.0 to pH 6.0, determined at 90° C. with starch as substrate.

A pullulanase of the invention can be characterized by having pullulanase activity at temperatures of from below 60° C. to approximately 100° C., having activity optimum at temperatures in the range 75°–85° C., determined at pH 5.5 with pullulan as substrate. The pullulanase can also be characterized by having pullulanase activity at pH values of from below pH 4.5 to approximately pH 9.8, having optimum in the range pH 5.0 to pH 6.0, determined at 90° C. with pullulan as substrate.

Determination of Amylase Activity

Amylase activity is determined by measuring the amount of reducing sugar released during the incubation with starch. One unit (U) of amylase activity is defined as the amount of amylase that releases 1μ mole of reducing sugar (as maltose standard) per min. under the following assay conditions: A 0.05 ml volume of 1% soluble starch is added to 0.05 ml of 0.1M sodium acetate buffer pH 5.5. 25 μl of enzyme solution are added to this mixture and the sample is incubated at 90° C. for 30 min. The reaction is stopped by cooling on ice, and the amount of reducing sugar is determined by dinitrosalicylic acid. Sample blanks are used to correct for nonenzymatic release of reducing sugar.

Determination of Pullulanase Activity

Pullulanase activity is determined by measuring the amount of reducing sugar released during the incubation with pullulan. One unit (U) of pullulanase activity is defined as the amount of pullulanase that releases 1μ mole of reducing sugar (as maltose standard) per min. under the following assay conditions: A 0.05 ml volume of 1% pullulan is added to 0.05 ml of 0.1M sodium acetate buffer pH 5.5. 25 μl of enzyme solution are added to this mixture and the sample is incubated at 90° C. for 30 min. The reaction is stopped by cooling on ice, and the amount of reducing sugar is determined by dinitrosalicylic acid. Sample blanks are used to correct for nonenzymatic release of reducing sugar.

Industrial Applications

The enzymes of this invention possess valuable properties allowing for various industrial applications. In particular the enzymes, in being thermostable, find potential application in the production of sweeteners and ethanol from starch. Conditions for conventional starch converting processes and liquefaction and/or saccharification processes are described in for instance U.S. Pat. No. 3,912,590 and EP patent publications Nos. 252,730 and 63,909.

The following example further illustrates the present invention, and it is not intended to be in any way limiting to the scope of the invention as claimed.

EXAMPLE 1

Cultivation

The strain *Fervidobacterium pennavorans*, DSM 7003, was recultured from glycerol-preserved cells using the medium recommended by the Deutsche Sammlung von Mikroorganismen (DSM). The microorganisms were grown in 1 liter batch cultures under the following conditions:

Medium $NH_4Cl$: 0.5 g/l
$MgSO_4.7H_2O$: 0.16 g/l
$K_2HPO_4.H_2O$: 1.6 g/l
$NaH_2PO_4.H_2O$: 1.0 g/l
yeast extract: 1.0 g/l
trypticase: 2.0 g/l Before autoclaving 10 ml/l of vitamin solution, 10 ml/l of Trace element solution, 0.05% cystein, HCl and 0.0002% of resazurine were added. Before inoculation, sterile $Na_2S.9H_2O$ was added at a concentration of 0.05%.

In the medium sulphur and tryptone were omitted and starch (0.5% w/v) was added as the only carbohydrate. Cultivation was performed at pH 6.5 and at 70° C. The cell density achieved in this medium was $\geq 10^8$ cells/ml. Anaerobic conditions were achieved during the preparation of media by sparging with $N_2$ and following the techniques as described by Balch in *Appl. Env, Microbiol.* 32, 1976, pp. 781–791.

After cultivation the culture fluid was centrifuged at 12.000×g for 30 min. at 4° C., and the cell free supernatant was concentrated up to 100-fold using an Amicon Ultrafiltration System. The cell pellet was resuspended in 50 mM sodium acetate buffer pH 5.5 and sonicated three times for 3 min. at 50% duty cycle by a BRANSON 450 sonifier. The cell debris was separated from the supernatant after centrifugation at 10.000×g for 30 min. at 4° C.

The following total activity (U) in both supernatant and cell extract was found:

Amylase activity: 2.5 U/l
Pullulanase activity: 4.5 U/l

The half-life, determined as the incubation time (min) at 85° C. after which 50% of the original activity is detected, gave the following results:

Amylase activity: 40 min
Pullulanase activity: 40 min

Temperature Optima

Temperature optima were determined by incubation of samples for 30 minutes at pH 5.5 at temperatures from 60° C. to 120° C. The incubation was conducted in closed Hungate tubes in order to prevent boiling of the solution.

FIG. 1 shows the result (Amylase (◻) and pullulanase (■)).

pH Optima

To determine pH optima, Universal buffer (Britten and Robinson) was used to obtain values from pH 4.0 to pH 10.0. Samples were incubated for 30 minutes at 80° C. at the pH in question.

Figure 2:
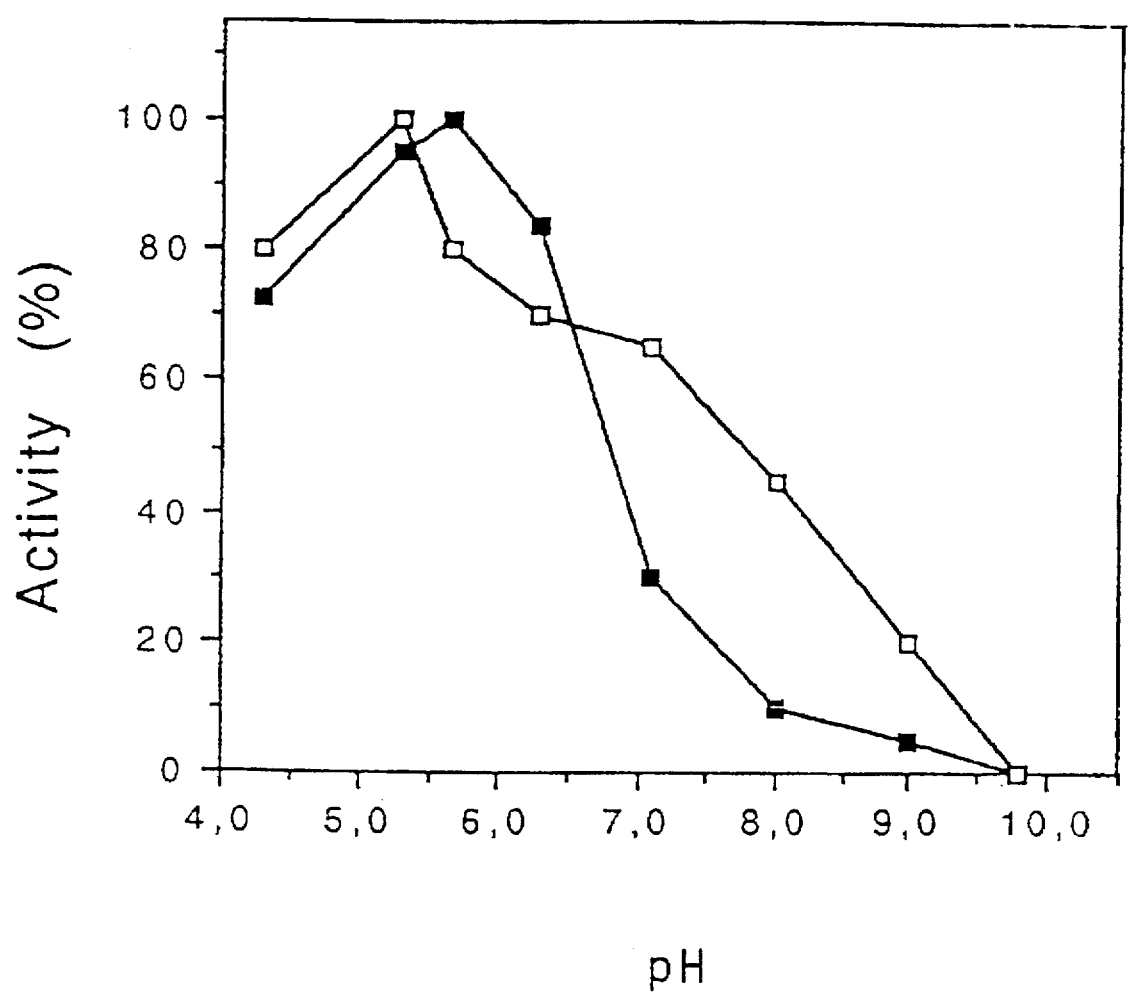
FIG. 2 shows the relative activity (% rel.) of an amylase (☐) and a pullulanase (■) of the invention at various pH, determined at 90° C. with starch and pullulan, respectively, as substrate.

FIG. 2 shows the result (Amylase (◻) and pullulanase (■)).

We claim:

1. An isolated amylase obtained from an amylase producing strain of the genus Fervidobacterium, having (a) a pH optimum in the range of 5.0 to pH 6.0, determined at 90° C. with starch as substrate, and (b) a temperature optimum in the range of 85° to 95° C., determined at pH 5.5 with starch as substrate.

2. The isolated amylase of claim 1, wherein the amylase producing strain is a *Fervidobacterium pennavorans* strain.

3. The isolated amylase of claim 2, wherein the amylase producing strain is *Fervidobacterium pennavorans*, DSM 7003.

4. A method for producing sweeteners, comprising reacting starch with an isolated amylase according to claim 1 wherein a sweetener is generated, and isolating the sweetener.

5. A method for producing ethanol, comprising reacting starch with an isolated amylase according to claim 1 wherein ethanol is generated, and isolating the ethanol.

* * * * *